United States Patent [19]

Agar

[11] Patent Number: 5,518,499

[45] Date of Patent: May 21, 1996

[54] INTRACAVERNOUS VASOACTIVE PHARMACOLOGICAL PUMP

[76] Inventor: Arif H. Agar, 12701 N. Pennsylvania Ave., Apt. 363, Oklahoma City, Okla. 73120

[21] Appl. No.: 467,214

[22] Filed: Jun. 6, 1995

[51] Int. Cl.⁶ .................................................. A61F 5/00
[52] U.S. Cl. .............................. 600/40; 623/11; 604/65; 604/891.1
[58] Field of Search ........................... 623/11; 604/65, 604/66, 67, 68, 891.1; 600/40

[56] References Cited

U.S. PATENT DOCUMENTS

| | | | |
|---|---|---|---|
| 4,604,994 | 8/1986 | Sealfon | 600/40 |
| 4,766,889 | 8/1988 | Trick et al. | 600/40 |
| 4,958,630 | 9/1990 | Rosenbluth et al. | 600/40 |

*Primary Examiner*—Paul B. Prebilic
*Attorney, Agent, or Firm*—R. William Graham

[57] ABSTRACT

The present invention is directed to a device for implantation into the scrotum of a male for aiding the male impotence, comprising, a housing containing a vasoactive agent, a conduit communicably connected to said housing and having a length such that when said housing is implanted in the scrotum, a terminal end of said conduit extends to a point in a corpus cavernosum of the penis and valve means associated with said housing and said conduit for opening communication therebetween which includes means associated with said housing for actuating said valve means, and wherein said valve means includes means for opening and closing said terminal end of said conduit.

6 Claims, 3 Drawing Sheets

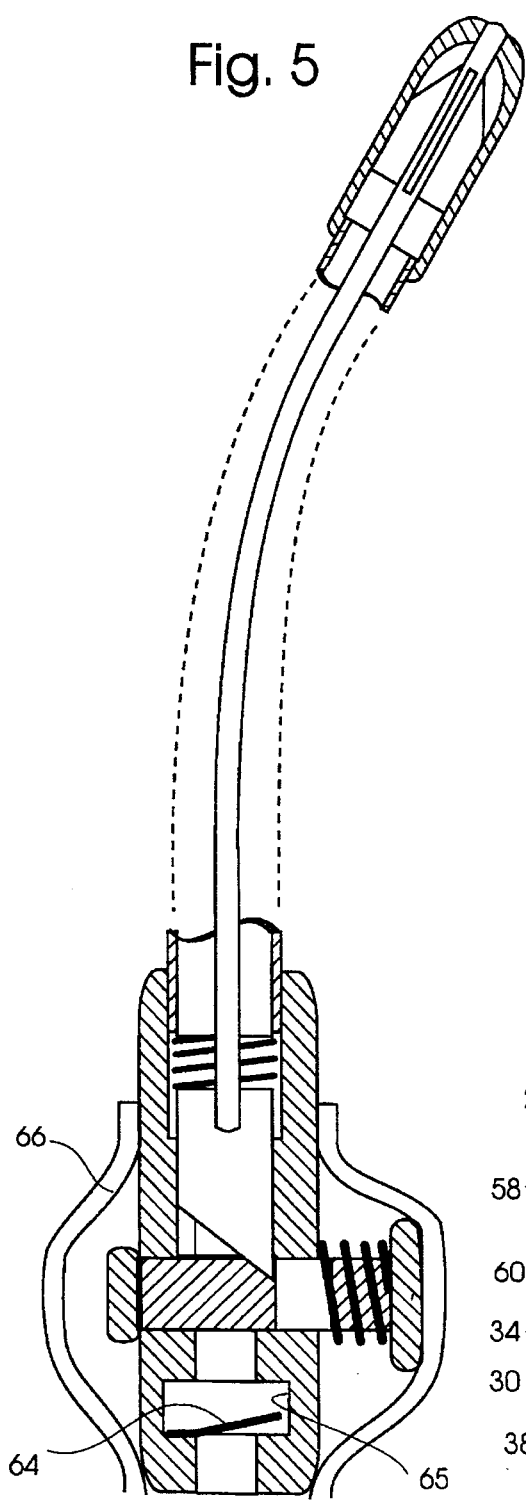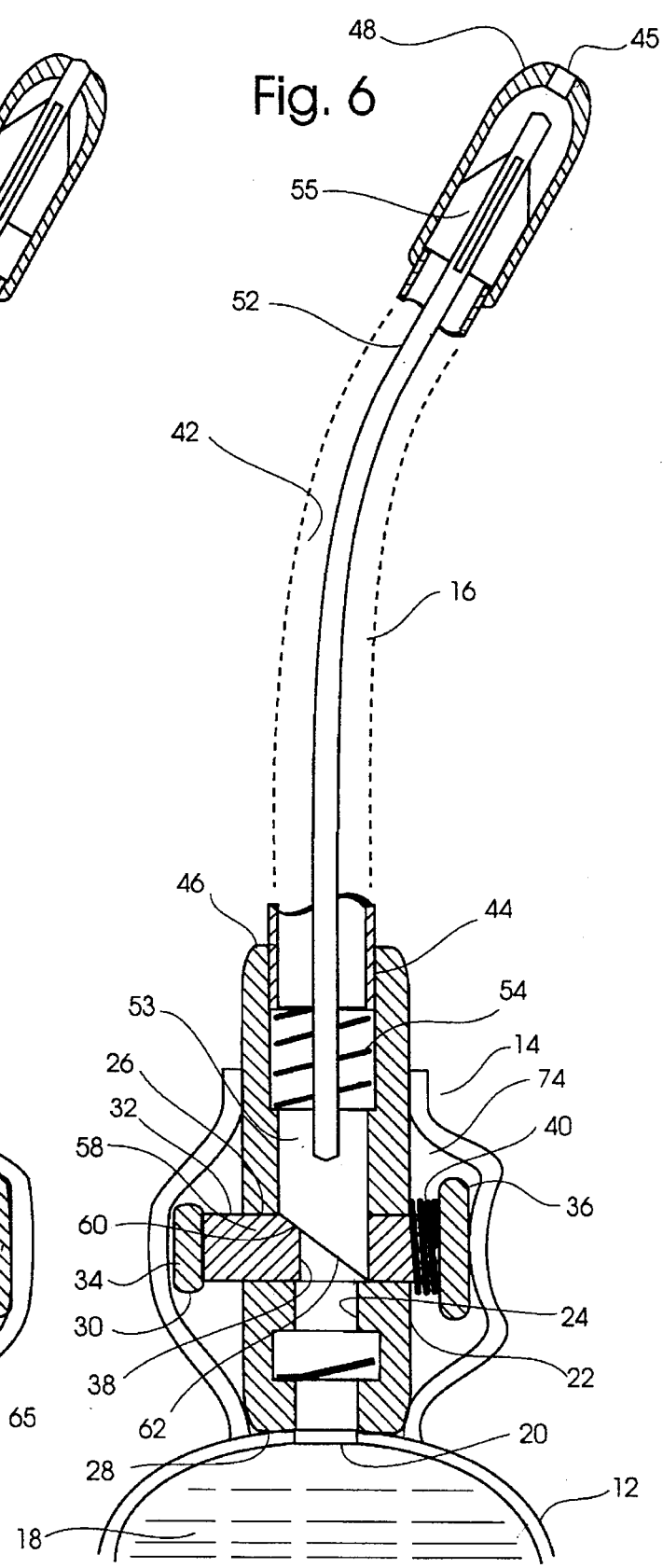

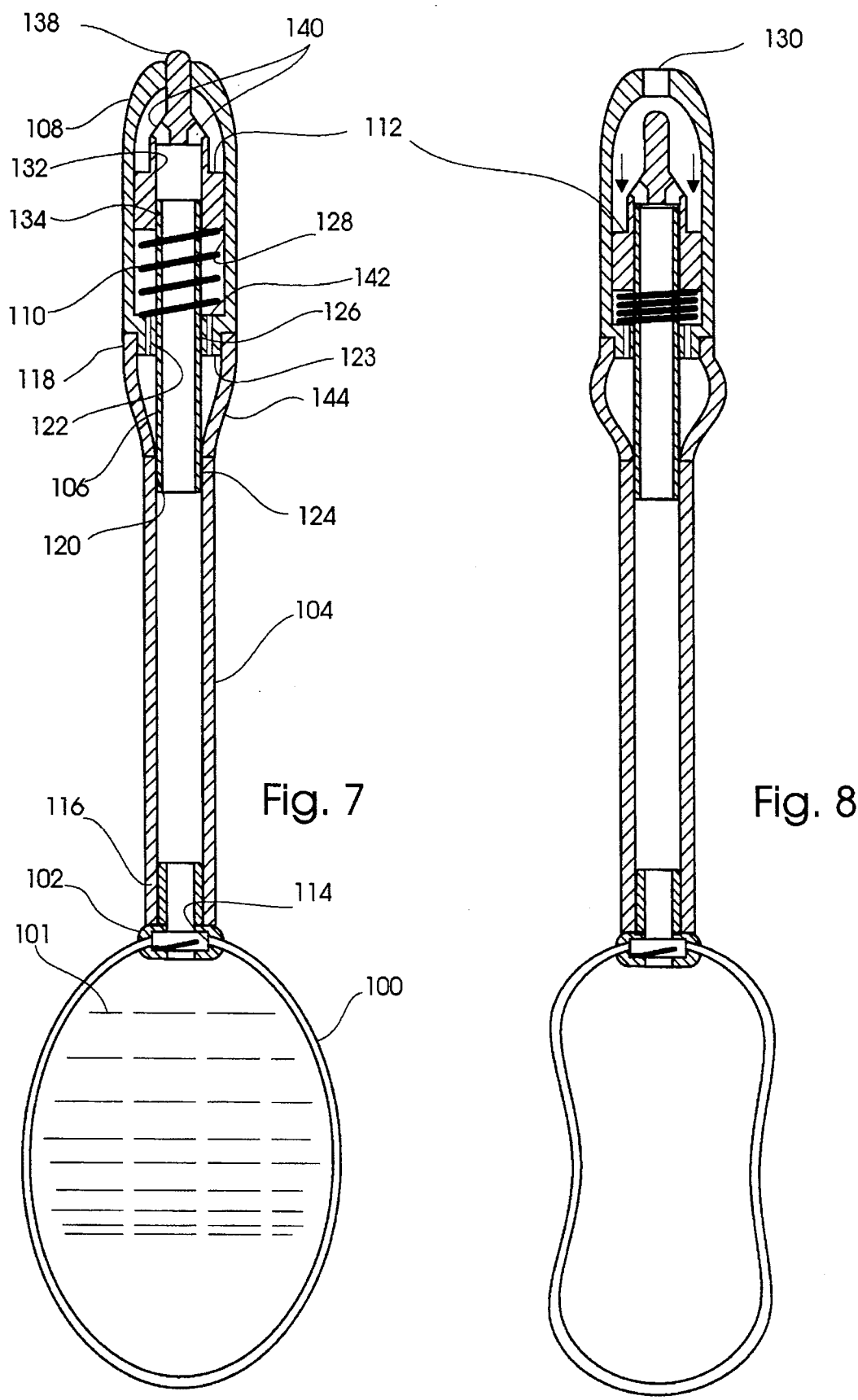

INTRACAVERNOUS VASOACTIVE PHARMACOLOGICAL PUMP

BACKGROUND OF THE INVENTION

1. Field of the Invention

The present invention relates generally to a device and method for delivering a pharmacological agent to the body, and more particularly, to a device and method for stimulating penile erection using a pharmacological agent.

2. Related Art

The field of male sexual dysfunction has witnessed dramatic improvements in the diagnosis and the management in the last decade. Attempts to discover aphrodisiacs and endeavors to improve sexuality appear to have been an inherent trait of mankind throughout the ages. Since the dawn of time, man has strived to combat the impotence with various medication. It is only recently that these efforts have borne some fruit.

Impotence affects nearly 10 million men in the Unites States. It creates mental stress and the sociologic distress both in the patient and his partner. Historically, the initial concern in the evaluation of an impotent man was to differentiate between psychogenic and organic impotence. In 50's and 60's the psychogenic impotence was considered to be the most common cause accounting for up to 90% of the cases. The advent of sophisticated technology has lead to critical discoveries in understanding of erectile function. The development of sensitive diagnostic armamentarium has made it possible to pinpoint an organic (and probably a treatable) cause in about 90% of the cases.

The penis consists of urethra and three erectile bodies: two corpora cavernosa and a corpus cavernosum. All of these structures have their own fascial sheaths and together they are covered with skin. Each corpus cavernosum has a thick fibrous layer, the tunica albuginea. The two corpora cavernosa constitute the main erectile tissue. Although they are depicted as separate bodies, they communicate with each other across the midline septum and act as a single erectile unit. They are filled with the helicine arteries, venous sinusoid, ventiles and emissary veins, nerves, muscle fibers, and trabeculae arising from the tunica albuginea. Close to the pubic symphysis the corpora split to from the crurae which are attached to the ischio-pubic rami.

The corpus spongiosum lies in the groove between the two corpora cavernosa on the ventral aspect. Its tunica albuginea is thin and at its distal end it expands to form the glans. Although it has erectile tissue it contributes only a little in the clinically significant erection. The urethra traverses through the entire length of the corpus spongiosum.

The three corpora are covered with deep fascia (Buck's fascia) that encloses the set of deep neuro-vascular structure. The superficial set of vessels, e.g., the dorsal vein of penis lies between the deep and the superficial fascia (Dartos fascia).

The skin of the penis is hairless. There are however sebaceous glands in the corona, the overhang rim of the glans, and the coronal sulcus that produce secretions called smegma. In an uncircumcised individual the redundant skin covers the glans as foreskin.

The blood supply of skin of the penis comes from the right and left inferior external pudendal vessel from the femoral arteries. The deeper structures are supplied by the common penile artery which is the continuation of the internal pudendal artery after it has given off the perineal branch. The emissary veins follow an oblique course through the tunica albuginea to drain into the deep dorsal veins which in turn drains into the prostatic (Santorini's) plexus. Three to four veins from the crura drain in to internal pudendal veins.

Penile erection is a complex phenomenon involving several factors. The animal and human studies have shown that the hemodynamic changes during erection consist of relaxation of smooth muscle of the arteriole and sinusoids, decreased resistance to blood flow; increased blood flow to the corpora cavernosa; expansion of lacunae of the sinusoid and distension of the tunica albuginea, compression of the ventiles and the emissary veins resulting in venous occlusion, increased pressure in the corpora cavernosa and penile erection.

These changes are mediated by neurotransmitters. The parasympathetic stimulation lead to erection by vasodilatation and the sympathetic stimulation causes detumescence by vasoconstriction. Acetylcholine, the cholinergic neurotransmitter, is presumed to act pre-junctionally leading to the release of a variety of still debated chemical mediators at the penile vascular smooth muscle neuromuscular junction. These mediators include nitric oxide, nonadrenergic noncholinergic neurotransmitter, vasoactive intestinal peptide and prostaglandin $E_1$.

Impotence is defined as failure to achieve and/or maintain erection sufficient for intercourse. Arbitrarily, repeated occurrence of this symptom for at least six months or more requires treatment.

For decades, impotence was associated with psychogenic causes. Organic etiology was first linked to sexual dysfunction in about 1923. At that time, it was still emphasized that the psychogenic etiology was the primary cause and that only 5% of impotence cases were secondary to organic diseases. With improved technologies in the area of diagnosis today, an organic cause can be found in most cases. Neurogenic, endocrinologic, and vasculogenic abnormalities account for 85% of impotence cases. Other causes include drugs and failure of the erectile tissue, e.g. Peyronie's disease. Psychogenic impotence makes only a small portion of the impotent population. The most common clinical conditions associated with erectile dysfunction include diabetes mellitus and hypertension.

The following methods are being presently practiced to treat the erectile dysfunction: Oral agents; Topical agents (Transcutaneous and transurethral); Hormones; Vacuum therapy; Intracavernous injection; and Penile prosthesis.

Oral agents, such as yohimbine chloride, an indole alkaloid derived from the bark of yohimbehe tree, has been considered an aphrodisiac for centuries in the western world. Scientific evaluation with double blind, placebo controlled studies has been performed only recently. These studies have shown a complete response of 20%, partial response of 23% and a failure rate of 57%.

Topical agents, such as nitroglycerin (NTG), a drug used for coronary artery disease for decades, has been used recently for the treatment of impotence. Aqueous based gel has been found to be rapidly absorbed through the penile skin. The mechanism of action is probably related to its ability to donate the nitric oxide (NO). Other NO donors, e.g., minoxidil have also been tried. Variable response rates have been published.

The advantage of the topical treatment is its ease of use and non-invasiveness. The quality of erection is poor. In addition it is associated with side effects, e.g., burning, headache, postural hypotension, syncope arid spousal headache via transvaginal absorption. Recently prostaglandin $E_1$ suppositories have been used transurethrally to produce erection. A multicenter trial is presently being carried out in the United States to assess the safety and the efficacy of this method.

Hormones, such as testosterone, given intra-muscularly in patients with low testosterone levels in the absence of other causes of erectile dysfunction may be helpful.

Vacuum therapy devices consist of a plastic cylinder, vacuum pump, connector tubing and elastic constriction band. Erection is achieved by creating negative pressure with the pump in the cylinder (which is applied on the penis), and maintained with the constriction band applied to base of the penis. Response rate of more than 90% has been reported. The device is relatively inexpensive and safe. The erection however is cold with a drop of penile skin temperature by 0.96° C. (the negative pressure produces pain and petechiae. Pain is also produced due to constricting band. The penis proximal to the constriction band is soft and pivots at the base. The major drawback is the lack of spontaneity.

Intracavernous injection is the modern pharmacological treatment and consists of injecting a vasoactive agent into the penis (corpus cavernosum) with a needle and a syringe under aseptic condition. The steps of treatment includes finding an optimum dose for an individual patient, educating the patient about the penile anatomy, and imparting training to inject with a sterile technique and self injection at home. It requires manual dexterity and bodily habitus which should not obstruct the patient's view of the penis as encountered in morbidly obese subjects.

Different medicines have been tried e.g., papaverine, phenoxybenzamine and prostaglandin $E_1$. Erection is achieved secondary to smooth muscle relaxation resulting in increased blood flow to the corpora cavernosa. Response rate of 80–100% have been achieved depending on the underlying cause. The quality of erection is very close to natural; it is warm and hard. The side effects include priapism, hematoma, inadvertent injection into the urethra, fibrosis, penile atigulation and parasthesias. Many patients (and their partners) refuse this modality due to needle phobia even those who use it suffer from the stigma of carrying a needle and syringe. Many patients complain of the lack of spontaneity and interruption of foreplay to inject.

Penile prosthesis or implants are placed in the corpus cavernosum. They are mainly of two distinct types: the malleable or the rigid prosthesis and multi-component inflatable prosthesis. The inflatable prosthesis have cylinders that are placed in the corpora cavernosa surgically. These are connected to reservoirs containing fluid. Erection is achieved by compression of the reservoir or a mechanical valve which leads to transference of fluid from the reservoir to the cylinders.

When properly implanted and limitation of the prosthesis are understood a very gratifying result is the norm. The quality of the erection is excellent in terms of rigidity but skin is cold. These device shave high mechanical failure rate. The complication include perforation of the corpora cavernosa, erosion, cylinder crossover, infection, penile curvature and glans bowing penile necrosis. The disadvantage of the procedure is the irreversibility and the need for major surgery. Additionally, such implants involve gross insult to the corpus cavernosum.

There remains a need for an improved device and method of treating male impotence. Moreover, a need remains for a device and method for causing penal erection in a more natural manner without interruption of sexual activity.

SUMMARY OF THE INVENTION

It is an object to improve treatment of male impotence.

It is another object to overcome the above described problems associated with treating impotence.

Still another object is to provide a scrotum implant device and method of for delivering a vasoactive agent into the corpus cavernosum in a manner which produces a more natural erection with minimal interruption in the sexual activity.

Accordingly, the present invention is directed to a device for implantation into a scrotum for aiding male impotence, comprising, a housing containing a vasoactive agent, a conduit communicably connected to said housing and having a length such that when the housing is implanted in the scrotum, a terminal end of the conduit extends to a point in a corpus cavernosum of the penis and valve means associated with the housing and the conduit for opening communication therebetween which includes means associated with the housing for actuating the valve means, and wherein the valve means includes means for opening and closing the terminal end of the conduit.

Other objects and features of the present invention will be readily apparent to those skilled in the art upon reading the drawings, specification and claims appended hereto.

BRIEF DESCRIPTION OF THE DRAWINGS

FIG. 5 shows a cross sectional view of part of an embodiment of the present invention with a valve in a closed position.

FIG. 6 shows a cross sectional view of part an embodiment of the present invention with a valve in an open position.

FIG. 7 shows a cross sectional view of another embodiment of the present invention with a valve in a closed position.

FIG. 8 shows a cross sectional view of another embodiment of the present invention with a valve in an open position.

DETAILED DESCRIPTION OF THE PREFERRED EMBODIMENTS

Figure 1:
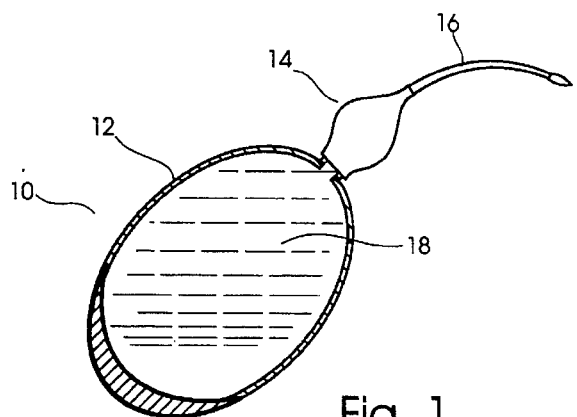
FIG. 1 is a sectional view of a housing of a device for an embodiment of the present invention.

Referring to the drawings, the device of the present invention is generally designated by the numeral 10. The device 10 includes a housing 12, a valve mechanism 14, a conduit 16 and a vasoactive agent 18 which will preferably be an FDA approved drug to suit a particular person's needs and which is easily stored within the housing 12.

Figure 2:
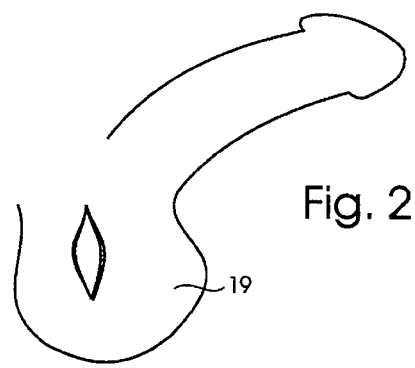
FIG. 2 shows an incision in a scrotum.
Figure 3:
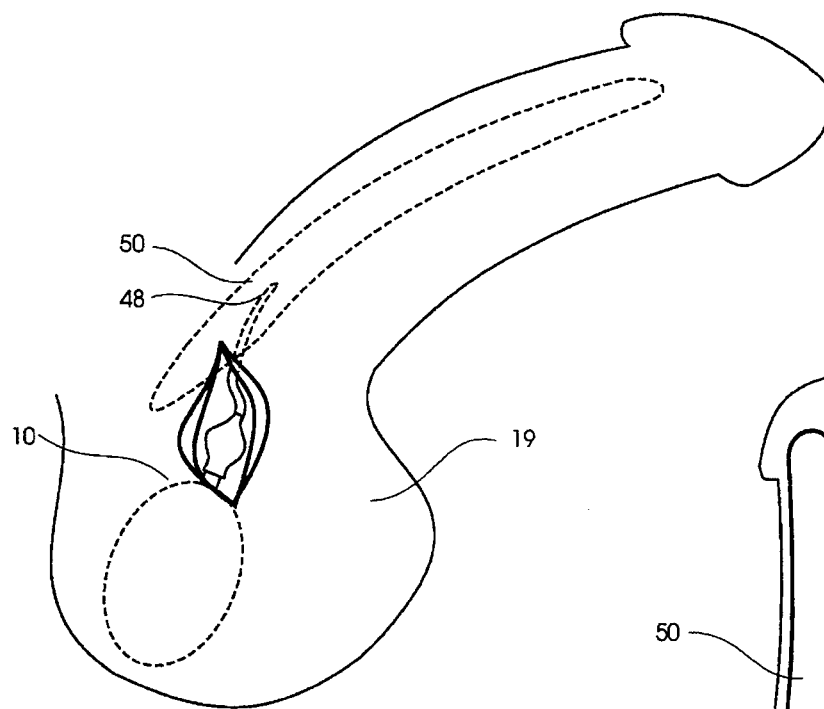
FIG. 3 shows an opening in the scrotum with the device of the present invention implanted therein.
Figure 4:
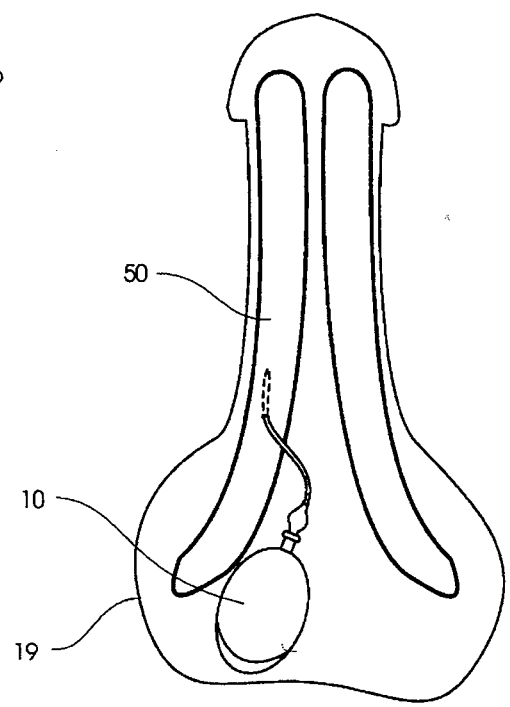
FIG. 4 is a representation of the device of the present invention implanted in the scrotum.

The housing 12 is of a shape which is suitable for implantation into a scrotum 19, for example, an elliptical shape, as shown in FIGS. 3 and 4. Implantation of the device is accomplished by delivering anesthesia to the patient, making an incision in the scrotum 19 as shown in FIG. 2. The incision should be deep into the dartos muscle, with the upper end of the incision leaving access to the corpus cavernosum 50. A pouch is developed to contain the housing 12. An empty housing 12 can be squeezed through the incision and placed into the pouch as shown in FIG. 3. The conduit 16 will be directed to the corpus cavernosum 50 and anchored to the penis by suture. The housing 12 is substantially liquid impermeable with the exception of a port surface 20. The housing 12 is preferably of a flexible material for aid in implantation and comfort to the user and which is needle permeable but self sealing upon needle removal. In this regard, the housing 12 is filled with the vasoactive agent 18 and the incision closed.

The valve mechanism 14 includes a generally hollow cylindrical member 22 having an axial chamber surface 24 therethrough and a radial bore surface 26 therethrough. The cylindrical member 22 is sealingly connected to the housing 12 at its one end 28 adjacent the port surface 20 of the housing 12 in a manner to permit fluid communication between the port surface 20 and axial chamber surface 24. The valve mechanism 14 further includes a plunger 30 which has an intermediate portion 32 having a diameter slightly less than a diameter of the bore surface 26 and slidably disposed within the bore surface 26, and ends 34 and 36 having a diameter larger than the diameter of the bore surface 26. The intermediate portion 32 includes a radial bore surface 38 substantially equivalent the diameter of the axial chamber surface 24 of the member 22. The intermediate portion 32 is of a length at least about that of a diameter of the cylindrical member 22 plus the diameter of the bore surface 26.

The radial bore surface 38 is disposed in the intermediate portion 32 such that when the end 34 abuts an outer surface of the cylindrical member 22, the radial bore surface 38 is not in communication with the axial chamber 24 and the valve mechanism 14 is in a closed position. A spring 40 is disposed about the intermediate portion 32 adjacent the end 36 to bias thereagainst and draw end 34 against the cylindrical member 22 and force away the end 36 from the cylindrical member 22. When the end 36 is manually forced toward the cylindrical member 22, the radial bore surface 38 comes into communication with the axial chamber 24, thus creating an open position in the valve mechanism 14.

The conduit 16 has an axial chamber surface 42 which at an end 44 is sealingly connected to an end 46 of the cylindrical member 22 such that the axial chamber surface 24 communicates with the axial chamber surface 42. A diameter of the axial chamber surface 42 at the end 44 is substantially equivalent the diameter of the axial surface chamber 24. The conduit 16 is configured such that the diameter of the axial chamber surface 42 at the end 48 is less than its diameter at end 44, and terminates into an open surface 45. The conduit 16 is preferably of a length such that when the housing 12 is implanted into the scrotum 19, its terminal end 48 reaches into a corpus cavernosum 50, as seen in FIGS. 3 and 4.

Returning to the valve mechanism 14 as depicted in FIGS. 5 and 6, also included is an elongated member 52 movably disposed within the conduit 16 having a blade member 53 extending from one end and centering side members 55 extending from the periphery adjacent the other end of the elongated member 52. Blade member 53 and side members 55 are of a thickness to readily permit fluid flow thereby within the chamber surfaces 24 and 42. Means 54 for biasing the elongated member 52 inwardly toward the radial bore surface 38 are disposed between the end 44 and blade member 53. The elongated member 52 is of a diameter approximately equal to the diameter of the open surface 45 of the end 48. The elongated member 52 is of a length such that when the valve mechanism 14 is closed, the elongated member 52 extends through to the open surface 45 at the terminal end 48 of the conduit 16 to close it off. In this regard, the elongated member 52 acts to plug the terminal end 48, preventing foreign material from entering therein.

The intermediate portion 32 of the plunger 30 is keyed to the cylindrical member 22 in a manner known in the art to prevent rotational movement of the intermediate portion 32 within the radial bore surface 26. Defined on one end 58 of the radial bore surface 38 is a beveled surface portion 60. The blade member 53 has a complimentary beveled surface portion 62 which slidably cooperates with the beveled surface 60. As the end 36 is pressed, the beveled surface portions 60 and 62 slidably move against one another permitting the elongated member 52 to move inwardly thus unplugging the terminal end 48. Because the elongated member 52 is less in diameter than all of the axial chamber surface 24, the radial bore surface 38 and the axial chamber surface 42, fluid communication is readily permitted thereabout. As the intermediate portion 32 moves to form an open position between the radial bore surface 38 and the axial chamber surface 24, the spring 40 acts as a stop for the end 36 and prevents the radial bore surface 38 from being in complete communication with the axial chamber surface 24 and, thus, the contacting of the blade member 53 with the beveled portion 60 prevents the elongated member 52 from passing through the radial bore surface 38.

Finally, the valve mechanism 14 includes a metering one way check valve 64 formed along the axial chamber surface 24 in a recessed surface 65 of the cylindrical member 22 between the radial bore surface 26 and end 28. The check valve 64 remains open under fluid pressure until back fluid pressure is exerted on the valve 64, at which time the valve 64 closes. The housing 12 may be squeezed in conjunction with the depressing of the plunger 30 to ensure delivery of the vasoactive agent 18. Upon release of the housing 12, a vacuum effect is created which draws the valve 64 to a closed position. Over time as the agent 18 is depleted, the housing 12 will be able to be squeezed into a smaller size which will provide the user with a gauge of amount of vasoactive agent 18 remaining in the housing.

Enclosing about the connections between the housing 12, valve mechanism 14 and the conduit 16 is a flexible non-permeable material 66 which is sealed in a manner to prevent foreign matter or liquid from contacting and potentially causing malfunction of the valve mechanism 14.

As depicted in FIGS. 7 and 8, an alternative embodiment is shown. In this embodiment, a hydraulic system is employed which includes a housing 100, vasoactive agent fluid 101, check valve 102, flexible conduit 104, a rigid conduit 106, rigid valve chamber 108, spring 110 and rigid valve member 112.

The housing 100 is of a material as that described above and has a port surface 114 to which is sealingly connected the check valve 102. The flexible conduit 104 has one end 116 sealingly connected to the check valve 102 and another end 118 sealingly connected to the rigid valve chamber 108.

The rigid conduit 106 has a diameter slightly less than the diameter of the inner surface 120 of the flexible conduit 104 and the diameter of an open surface 122 of a collar 123 of the rigid valve chamber 108. The rigid conduit 106 has an end 124 sealingly connected to a portion of inner surface 120 of the flexible conduit 104 and extends through into the rigid valve chamber 108 having an intermediate portion 126 sealingly connected to the open surface 122.

An inner wall surface 128 of the rigid valve chamber 108 is recessed from the collar 123 and terminates into a small open surface 130. The rigid valve member 112 has a cylindrical portion 132 which is sealingly slidably disposed on an end 134 of the conduit 106. The spring 110 is disposed about the rigid conduit 106 biasing against the collar 123 and the cylindrical portion 132.

The valve member 112 includes a nose portion 138 of a diameter and size to substantially sealably fit within the open surface 130 and act as a plug when disposed therein. Adjacent the nose portion 138 are port surfaces 140 to allow fluid communication from the port surface 114 through to the open surface 130. The collar 123 includes port surfaces 142 to allow air communication between an air pocket formed between an expanded portion 144 of the flexible conduit 104 and the conduit 106 and an air pocket formed between the cylindrical portion 132, inner wall surface 128 and rigid conduit 106.

Normally, the spring 110 biases the rigid valve member 112 such that the nose portion 138 plugs the open surface 130. Thus, the device is in a closed position, as seen in FIG. 7.

As the housing 100 is squeezed, the fluid 101 exerts pressure on the cylindrical portion 132 which overcomes the spring's 136 force thus driving the valve member 112 inward and removing the nose portion 138 from the open surface 130 thus creating an open position. As fluid flows through the open surface 130, the pressure drops and the spring 110 forces the valve member 112 outward to a closed position. The check valve 102 operates in a similar fashion to the check valve 64 described above.

It will be readily apparent to those skilled in the art that other modifications, derivations and improvements may be formed without departing from the scope of the invention. Accordingly, the claims appended hereto should be accorded their fullest scope of protection including any such modifications, derivations or improvements.

What is claimed is:

1. A device for implantation into a scrotum of a penis for aiding male impotence, comprising:

a housing containing a vasoactive agent;

a conduit communicably connected to said housing and having a length such that when said housing is implanted in the scrotum, a terminal end of said conduit extends to a point in a corpus cavernosum of the penis; and valve means associated with said housing and said conduit for opening and closing communication therebetween which includes means associated with said housing for actuating said valve means, and wherein said valve means includes means for opening and closing said terminal end of said conduit.

2. The device of claim 1, wherein said valve means includes metering means for metering an amount of said vasoactive agent which is communicated upon actuation of said actuating means.

3. A method for treating male impotence, which includes:

a) implanting in a scrotum a device having a housing containing a vasoactive agent, a conduit communicably connected to said housing and having a length such that when said housing is implanted in the scrotum a terminal end of said conduit extends to a point in a corpus cavernosum of a penis and is implanted from the scrotum to the corpus cavernosum, and valve means associated with said housing and said conduit for opening communication therebetween which includes means disposed in the scrotum for actuating said valve means, and wherein said valve means includes means for opening and closing said terminal end of said conduit; and b) actuating said actuating means to cause said valve means to open said terminal end of said conduit and said vasoactive agent to flow to the corpus cavernosum.

4. The method of claim 3, wherein the step (a) is further characterized such that said device includes metering means for metering an amount of said vasoactive agent which is communicated upon actuation of said actuating means.

5. A device for implantation into a scrotum of a penis for aiding male impotence, comprising:

a housing containing a vasoactive agent;

a conduit communicably connected to said housing and having a length such that when said housing is implanted in a scrotum, a terminal end of said conduit extends to a point in a corpus cavernosum of the penis; and valve means associated with said housing and said conduit for opening communication therebetween which includes means disposed in the scrotum for actuating said valve means, and wherein said valve means includes means for opening and closing said terminal end of said conduit.

6. The device of claim 5, wherein said valve means includes metering means for metering an amount of said vasoactive agent which is communicated upon actuation of said actuating means.

\* \* \* \* \*

UNITED STATES PATENT AND TRADEMARK OFFICE
CERTIFICATE OF CORRECTION

PATENT NO.  : 5,518,499
DATED       : May 21, 1996
INVENTOR(S) : Arif H. Agha

It is certified that error appears in the above-indentified patent and that said Letters Patent is hereby corrected as shown below:

On the title page, item [76], the name "Agar" should be removed and replaced with --Agha--

Signed and Sealed this

Twenty-fourth Day of September, 1996

Attest:

BRUCE LEHMAN

Attesting Officer

Commissioner of Patents and Trademarks